US 6,689,051 B2

(12) United States Patent
Nakada et al.

(10) Patent No.: US 6,689,051 B2
(45) Date of Patent: Feb. 10, 2004

(54) ENDOSCOPE HOOD FOR MUCOUS MEMBRANE RESECTION

(75) Inventors: Mamoru Nakada, Hachioji (JP); Chika Shiro, Hachioji (JP)

(73) Assignee: Olympus Corporation, Tokyo (JP)

( * ) Notice: Subject to any disclaimer, the term of this patent is extended or adjusted under 35 U.S.C. 154(b) by 219 days.

(21) Appl. No.: 09/861,684

(22) Filed: May 21, 2001

(65) Prior Publication Data

US 2001/0053909 A1 Dec. 20, 2001

(30) Foreign Application Priority Data

May 26, 2000 (JP) .................................. P2000-156804
Jan. 26, 2001 (JP) .................................. P2001-018993

(51) Int. Cl.[7] ............................................. A61B 1/00
(52) U.S. Cl. ................................. 600/140; 600/129
(58) Field of Search ............................ 606/49, 46, 47; 600/104, 127, 129, 130, 153, 175, 156, 159, 140, 139

(56) References Cited

U.S. PATENT DOCUMENTS

| 5,891,013 A | * | 4/1999 | Thompson ................... 600/104 |
| 5,968,056 A | * | 10/1999 | Chu et al. .................... 606/140 |
| 5,976,073 A | * | 11/1999 | Ouchi ........................ 600/129 |
| 6,059,719 A | * | 5/2000 | Yamamoto et al. ......... 600/127 |
| 6,068,603 A | * | 5/2000 | Suzuki ....................... 600/565 |

FOREIGN PATENT DOCUMENTS

JP 6-75402 10/1994

\* cited by examiner

*Primary Examiner*—Michael Peffley
*Assistant Examiner*—Aaron Roane
(74) *Attorney, Agent, or Firm*—Scully, Scott, Murphy & Presser (57) ABSTRACT

A hood for an endoscope has a cap part detachably mounted on the end portion of the insertion part of an endoscope. An opening communicates with the inside of the cap part, at the end of a flexible tube connected to the opening. Into the flexible tube, such an endoscopic treating instrument as a high frequency snare is inserted.

24 Claims, 5 Drawing Sheets

ENDOSCOPE HOOD FOR MUCOUS MEMBRANE RESECTION

CROSS-REFERENCE TO RELATED APPLICATIONS

This application is based upon and claims the benefit of priority from Japanese Patent Applications No. 2000-156804 filed on May 26, 2000 and No. 2001-18993 filed on Jan. 26, 2001 in Japan, the entire contents of which are incorporated by reference.

BACKGROUND OF THE INVENTION (1) Field of the Invention

The present invention relates to a hood for an endoscope used for endoscopy and endoscopic operations. More particularly, the present invention relates to an endoscope hood which is approximately cylindrical and installed on the distal end of the endoscope insertion part. In the hood, a mucous membrane is absorbed and swells. A high frequency snare cuts the basal portion of the swelling mucous membrane.

(2) Description of the Prior Art

In the prior art, an operation by means of an endoscope is done without cutting an abdominal wall open. A high frequency snare is introduced into the body through a channel of an endoscope is used for early cancer of gullet and stomach, in order to cut a mucous membrane of a diseased part.

Generally in such an endoscopic mucosal resection, a subcylindrical hood is installed on the distal end of the insertion part of an endoscope. A mucous membrane is drawn into the hood and swells. The basal part is caught and cut with a high frequency snare. It is important to precisely locate a wire of a high frequency snare on the basal part of an upheaval-shaped mucous membrane drawn in an endoscope hood.

Japanese Utility Model Laid-Open Publication No. 6-75402 discloses a hood for an endoscope comprising a transparent hard cap part and a connection part connecting the cap part to the end portion of an endoscope and nails which protrude from the end portion of the cap part. In Japanese Patent Laid-Open Publication No. 9-187415, an endoscope has a channel located outside the transparent cylindrical cap part.

(2) Description of the Related Art

In Japanese Utility Model Laid-Open No. 6-75402 bulletin, a high frequency snare passes through an endoscope channel. In this case, an end aperture part of the endoscope channel is spaced inwardly from the internal surface of a hood. Accordingly, it is difficult to widen the loop of the high frequency snare introduced into the hood through the endoscope channel.

Furthermore, a high frequency snare through an endoscope channel and other endoscopic treating instruments cannot be used simultaneously. In particular, it cannot be confirmed whether or not a high frequency snare catches muscular coats, since the high frequency snare and an ultrasonic probe cannot pass through simultaneously. In addition, suction power becomes weak since suction is done with an endoscope channel blocked by a high frequency snare. Therefore, a mucous membrane does not swell enough. In Japanese Patent Laid-Open No. 9-187415 bulletin, before an endoscope is inserted into the body, a high frequency snare is inserted into a channel disposed on the outside of a cap part. The loop of the high frequency snare is widened and held outside the cap part. In this case the loop of the snare wire is widened and positioned around the cap part outside the body. Therefore, the endoscope has to be pulled out of the body in order to hang the snare again. This makes the operation more difficult. In addition, the loop of the snare wire, when widened and hung outside the cap part is hard to come off the cap part.

SUMMARY OF THE INVENTION

Therefore, it is an object of the present invention to provide a hood for an endoscope with which endoscopic mucosal resection is safely and easily operated using a high frequency snare.

Accordingly, the present invention provides a hood for an endoscope having a preferably transparent and substantially cylindrical cap part which defines a cavity and is mounted on the end portion of an endoscope insertion part; an endoscope mounting part for detachably fixing the cap part to the end portion of the insertion part of the endoscope; and a flexible tube whose end portion is connected to an opening communicating with the cavity of the cap part so that an endoscopic treating instrument is removably inserted. Due to the above-mentioned structure, endoscopic treating instruments such as an ultrasonic probe are brought into the body through a channel of the endoscope and a high frequency snare is brought through the flexible tube. Thus, by using the ultrasonic probe or the like, it can be confirmed how the high frequency snare binds a mucous membrane and muscular coats so that the mucous membrane is resected more safely. In addition, an operation becomes easier, since an operator can use the high frequency snare through the flexible tube and such endoscopic treating instruments through endoscope channels as an injection needle and a high frequency knife which are necessary to resect a mucous membrane.

Furthermore, the looping of a snare wire becomes easier, since the looping can be repeated in the cap part without pulling out the endoscope. Also, since a channel of the endoscope can be empty, a mucous membrane is surely sucked and swells.

BRIEF DESCRIPTION OF THE DRAWINGS

These and other features, aspects, and advantages of the apparatus and methods of the present invention will become better understood with regard to the following description, appended claims, and accompanying drawings where:

DETAILED DESCRIPTION

The embodiments of the invention will be described with reference to the accompanying drawings.

Figure 1:
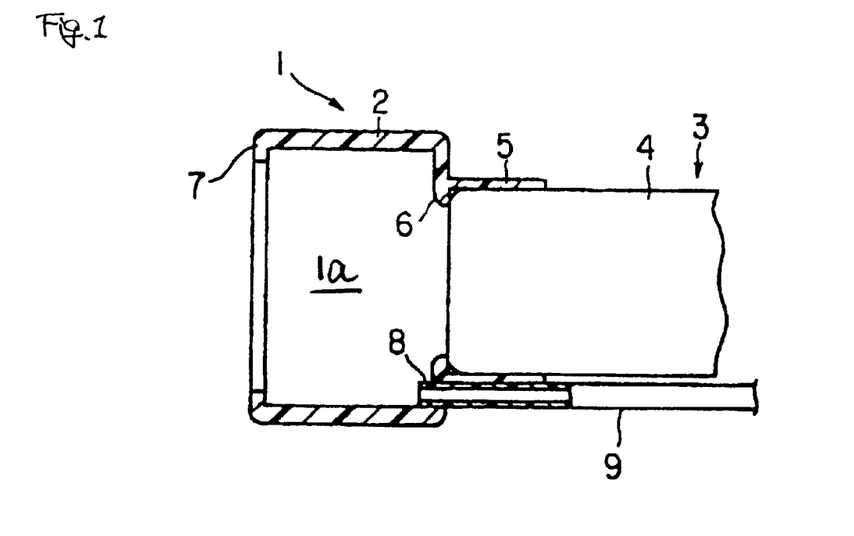
FIG. 1 is a section view showing a hood for an endoscope according to the first embodiment of the invention.
Figure 2:
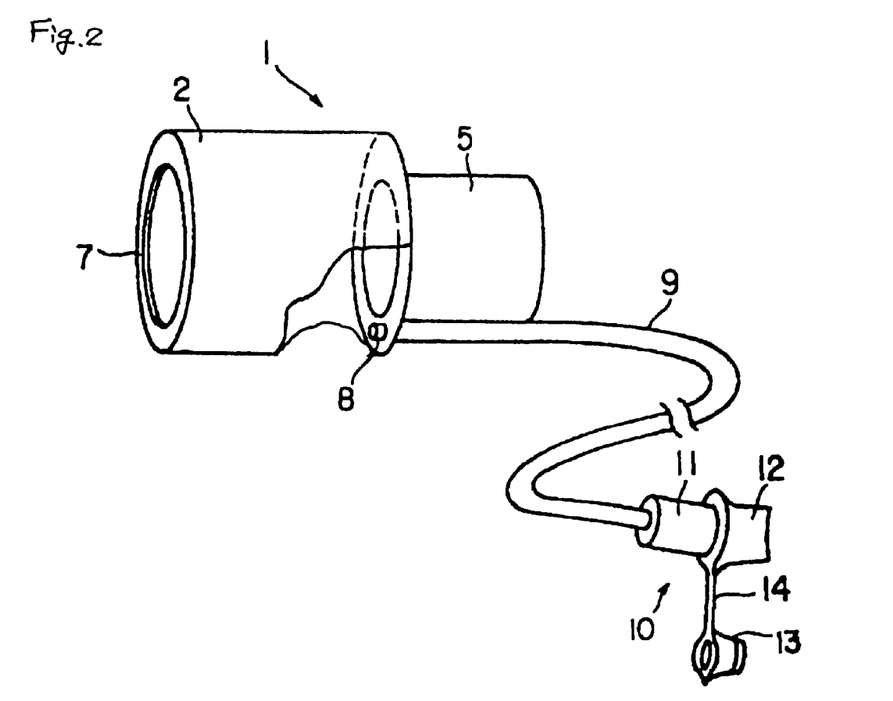
FIG. 2 is a perspective view showing the hood for an endoscope according to the first embodiment of the invention.

FIGS. 1 and 2 show a hood 1 for an endoscope according to a first embodiment of the invention. The hood 1 for an endoscope comprises a cap part 2 defining a cavity 1a which in a preferred implementation is approximately cylindrical and transparent. The hood 1 further comprises an endoscope mounting part 5 (alternatively referred to herein as a "fixing part") which is approximately cylindrical and detachably fix to the hood 1 on the end portion of an insertion part 4 of an endoscope 3. The cap part 2 is approximately cylindrical with the outer diameter 18 mm, the inner diameter 16 mm and the length 14 mm. The endoscope mounting part 5 is approximately cylindrical with the outer diameter 13 mm, the inner diameter 12 mm and the length 10 mm.

On the end portion of the endoscope mounting part 5, an endoscope stop 6 protrudes toward the inner center. The length of the endoscope stop 6 is preferably about 0.5 mm. In order to fix the hood 1 to the endoscope 3, the end of the insertion part 4 of the endoscope 3 is inserted into the inner part of the endoscope mounting part 5. As shown in FIG. 1, the endoscope 3 is pushed until the end of the insertion part 4 of the endoscope 3 runs into the endoscope stop 6. The endoscope stop 6 prevents the end of the insertion part 4 of the endoscope 3 from going into the cap part 2, and the endoscope mounting part 5 of the hood 1 for an endoscope is fixed on the end of the insertion part 4 of the endoscope 3.

Figure 4:
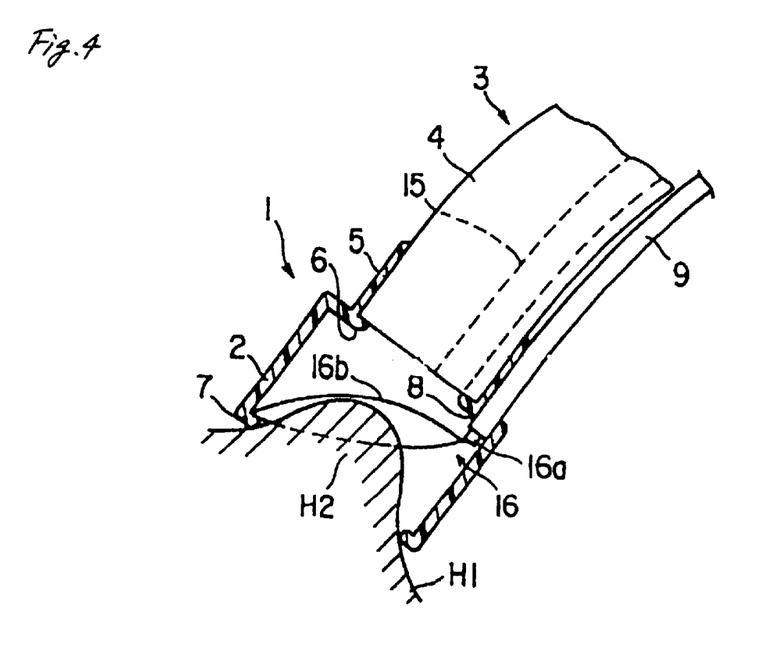
FIG. 4 is a section view showing that a snare wire is about to loop around the mucous membrane in the hood for an endoscope according to the first embodiment of the invention.

Also on the end portion of the cap part 2, a flange 7 protrudes towards the center of the hood 1. The length of the flange is preferably 0.8 mm. As shown in FIG. 4, a snare wire 16b is disposed in the cavity 1a from a sheath 16a of a high frequency snare 16. The snare wire 16b engages with the flange 7 which contains the snare wire 16b in the cavity 1a.

An opening 8 communicating with the cavity 1a of the cap part 2 is formed in a flange between the proximal end of the cap part 2 and the distal end of the endoscope mounting part 5. Outside the endoscope mounting part 5 is arranged a flexible tube 9 into which a treating instrument such as the high frequency snare 16 can be inserted. The end portion of the flexible tube 9 is connected to the opening 8. The end portion of the flexible tube 9 is fixed to the endoscope mounting part 5 and the cap part 2 in an airtight state by means of bonding, welding or the like. The end of the flexible tube 9 opens into the cavity 1a of the cap part 2.

The longitudinal axis of the flexible tube 9 and the axis of the cap part 2 are almost parallel at the connection part of the flexible tube 9 and the cap part 2. The opening end of the flexible tube 9 is adjacent to the inner wall of the cap part 2.

Furthermore, the hood 1 is preferably formed of thermoplastic elastomer whose transmittance is 90% or more and Shore hardness is 82. However, material of the hood 1 is not limited to the above thermoplastic elastomer. The material may be a flexible transparent resin which comprises a block copolymer (A) formed of polymer block (a) mainly made from vinyl aromatic compound and polymer block (b) mainly made from conjugate diene compound, and an acrylic resin (B) whose main component is methyl methacrylate, and a composition (C) whose main component is at least one thermoplastic resin. More particularly, the component of polymer block (a) is styrene and the component of polymer block (b) is isoprene, preferably. And the resin of (B) is preferably an acrylic resin being a copolymer of methyl methacrylate-acrylic acid. The thermoplastic resin of (C) is preferably styrene-acrylonitrile resin.

The above-mentioned resin has excellent biocompatibility. The resin is unpigmented and has a transmittance such that field of view is not affected in the endoscope 3. The resin also has a hardness such that the hood 1 is not deformed much when the hood 1 is pressed to a mucous membrane and a mucous membrane is sucked in the hood 1.

The outer diameter of the cap part 2 of the hood 1 is about 16–20 mm in order to alleviate a patient's pain. The inner diameter of the cap part 2 is about 14–18 mm so that a mucous membrane will not be cut unnecessarily large. The thickness of the cap part 2 is about 0.5–2 mm so that the cap part 2 will not be deformed much when the hood 1 is pressed to a mucous membrane and a mucous membrane is sucked in the hood 1. As a result of the above, a preferable cap part 2 of the hood 1 has the outer diameter of about 18 mm and the inner diameter of about 16 mm and the thickness of about 1 mm.

The rim of the cap part 2 is formed in a plane vertical to the insert direction of the endoscope 3. The rim may be formed obliquely to the insert direction.

The inner diameter of the endoscope mounting part 5 of the hood 1 is about 6–16 mm since the inner diameter needs to be fit to the outer diameter of the endoscope 3. The thickness of the endoscope mounting part 5 is about 0.5–1 mm so as to be easily mounted to the endoscope 3 and to be easily molded. The endoscope mounting part 5 should not fall away when the endoscope 3 to which the hood 1 is mounted is inserted into a body cavity nor prevent the endoscope 3 from bending. Therefore, the length of the endoscope mounting part 5 in the axial (or insertion) direction of the endoscope 3 is preferably about 3–10 mm. As a result of the above, a preferable endoscope mounting part 5 has the thickness of 0.7 mm and the length of 10 mm.

The width of the flange 7 provided on the end of the cap part 2 is at least 0.3 mm since the width needs to be longer than the diameter of the snare wire 16b. However, the longer the width becomes the less a mucous membrane is sucked and the amount of mucous membrane to be cut is reduced. Therefore, the width is, at most, shorter than 2 mm, and preferably about 0.8 mm.

The endoscope stop 6 is provided in the end portion of the endoscope mounting part 5. The endoscope stop 6 needs to have a length in the radial direction of the endoscope 3 such that the end of the endoscope 3 to which the endoscope mounting part 5 is mounted stops even if the cavity wall presses on the endoscope 3 which is inserted. Meanwhile, if the endoscope stopper 6 is too long, field of view is obstructed. Accordingly, the length of the endoscope stop 6 ranges from 0.3 mm to 1 mm, and is about 0.5 mm preferably.

The length of the flexible tube 9 along the insertion part 4 is preferably almost the same as or longer than that of the insertion part 4 of the endoscope 3. Material for the flexible tube 9 is preferably flexible. For example, such soft synthetic resins as fluororesin, polyvinyl chloride, polyurethane, polyethylene are preferable, so that the flexible tube 9 will neither prevent the insertion part 4 of the endoscope 3 from bending nor injure tissues of alimentary canals in the body. The inner diameter of the flexible tube 9 is preferably 1.0–4 mm, more preferably about 2.9 mm so that typical endoscopic treating instruments can be inserted therein.

An airtight valve 10 is preferably provided at the proximal end of the flexible tube 9. The airtight valve 10 preferably comprises a body portion 11, a forceps tap 12, a cap 13, and a connecting belt 14. The forceps tap 12 is fixed to the body portion 11 fixed to the proximal end of the flexible tube 9. The cap 13 is detachably attached to the forceps tap 12. The connecting belt 14 connects the cap 13 and the forceps tap 12. The airtight valve 10 is set airtight not only when nothing is inserted into the flexible tube 9 but also when endoscopic treating instruments are inserted. This prevents human waste and mucus from leaking through the flexible tube 9 to the proximal side even if the endoscope 3 remains inside the body.

The operation of the hood 1 for an endoscope according to the first embodiment will now be explained with reference to FIGS. 3–6. The explanation is for the process of resecting a mucous membrane H1 with the endoscope 3 to which the hood 1 according to the first embodiment is mounted.

Figure 3:
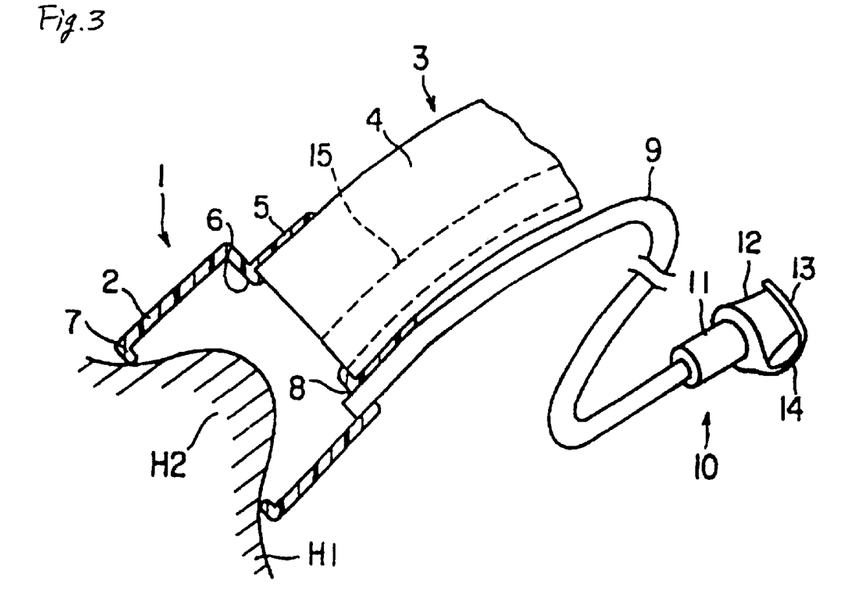
FIG. 3 is a section view showing a mucous membrane sucked by a cap part of the hood for an endoscope according to the first embodiment of the invention.

First, the hood 1 is mounted on the end of the insertion part 4 of the endoscope 3 until the insertion part 4 abuts the endoscope stop 6. The flexible tube 9 is then fixed along the insertion part 4 of the endoscope 3 with a medical tape or the like. While this state is kept, the insertion part 4 of the endoscope 3 is inserted into the body, operated with an operation part which is not shown. The opening end of the cap part 2 of the hood 1 is moved to an objective mucous membrane H2 to be resected.

As shown in FIG. 3, the opening end of the cap part 2 of the hood 1 for an endoscope is then pressed on the mucous membrane H1 in the vicinity of an objective mucous membrane H2. While this state is kept, vacuum is applied to the cavity 1*a* through the channel 15 of the endoscope 3 by a suction device (not shown). Due to negative pressure in the cavity 1*a*, the mucous membrane H1 gets sucked in the cavity 1*a* of the cap part 2 and a resected part H2 of the mucous membrane H1 swells therein. Then, the abovementioned airtight valve 10 prevents human waste and mucus from leaking to the proximal side through the flexible tube 9. Moreover, external air is prevented from getting in the cap part 2 of the hood 1 and the suction of the mucous membrane H1 is not obstructed.

After the opening end of the cap part 2 is pressed on the mucous membrane H1, an injection needle may be protruded into the inside of the cap part 2 through the flexible tube 9 or the channel 15 of the endoscope 3 in order to inject physiological saline between the resected part H2 of the mucous membrane H1 and muscular coats H3. This enables the resected part H2 of the mucous membrane H1 to easily swell from the applied suction.

At this point, the high frequency snare 16 is inserted into the flexible tube 9 through the airtight valve 10 which is provided outside the body, until the tip of the high frequency snare 16 protrudes up to the cavity 1*a* of the cap part 2.

Figure 5:
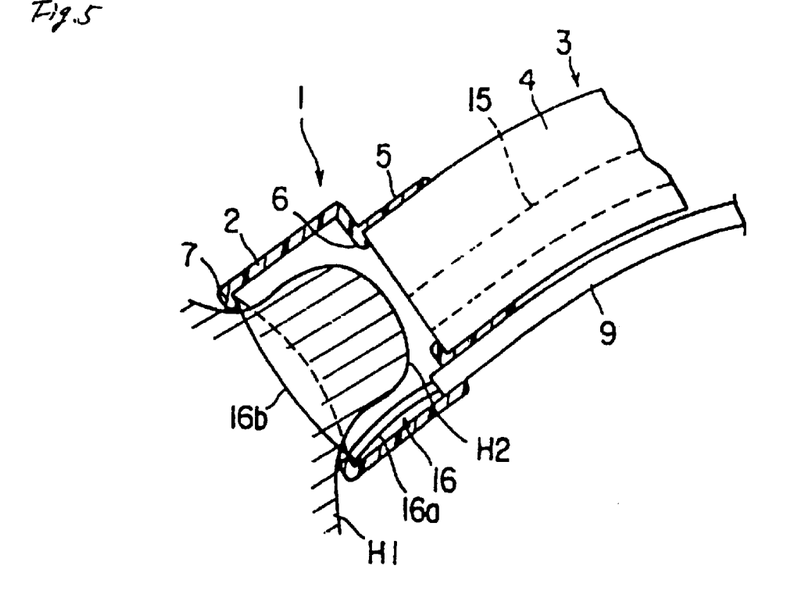
FIG. 5 is a section view showing that the snare wire loops around the mucous membrane in the hood for an endoscope according to the first embodiment of the invention.

Next, the snare wire 16*b* is let out of the sheath 16*a*. while the tip portion of the snare wire 16*b* is placed on the flange 7, the snare wire 16*b* is pushed out, as shown in FIG. 4. This operation allows the loop of the snare wire 16*b* to widen along the inner surface at the end of the cap part 2. Consequently, as shown in FIG. 5, the snare wire 16*b* can be easily placed over the bottom of the resected part H2 which is the swelling part of the mucous membrane H1.

Further suction can then be applied to the cavity 1*a* while the snare wire 16*b* placed over the bottom of the resected part H2 to allow the resected part H2 to continue to swell into the cavity 1*a* of the cap part 2, and substantially fill the cavity 1*a*.

Figure 6:
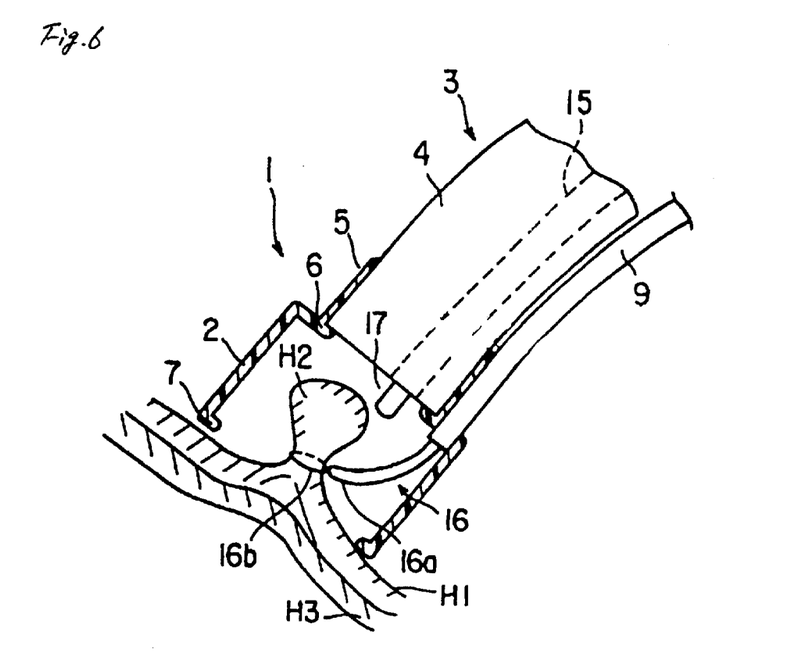
FIG. 6 is a section view showing that the snare wire tightly binds the mucous membrane in the hood for an endoscope and that the state of the mucous membrane and muscular coats is confirmed with an ultrasonic probe.

As shown in FIG. 6, the snare wire 16*b* is then drawn into the sheath 16*a* to tightly bind the bottom of the resected part H2 of the mucous membrane H1. An ultrasonic probe 17 inserted into the channel 15 can then be used to observe the mucous membrane H1 and the muscular coats H3 to check whether the muscular coats H3 are snared by the snare wire 16*b*. Those skilled in the art will appreciate that the endoscope hood 1 of the present invention makes the resection of the mucous membrane H1 safe. The resection of the mucous membrane H1 with the muscular coats H3 snared by the snare wire 16*b* may cause perforating and bleeding.

If it is determined that the muscular coats H3 are not captured by the snare wire 16*b,* in order to resect the mucous membrane H1, a high-frequency current is applied to the snare wire 16*b*. After this, the ultrasonic probe 17 is pulled out of the channel 15 of the endoscope 3. A suction device (not shown) sucks the mucous membrane 1 through the channel 15, so that the resected mucous membrane H2 is taken outside the body while the endoscope 3 remains inside the cap part 2. If the mucous membrane 1 is resected in such a way that a resected part can pass through the channel 15, the resected part may be sucked out.

Since the hood 1 according to the embodiment has the flexible tube 9 as a channel for endoscopic treating instruments other than the channel 15 of the endoscope 3, the high frequency snare 16 inserted into the flexible tube 9 and the ultrasonic probe 17 inserted into the channel 15 can be used at the same time, without providing another channel in the endoscope 3. This enables the mucous membrane 1 to be safely resected, since the ultrasonic probe 17 can be used to observe how the wire binds the mucous membrane H1 and the muscular coats H3.

Moreover, such endoscopic treating instruments as an injection needle or a high frequency knife may also be necessary in the resection of the mucous membrane H1. Since these instruments can be used with the high frequency snare 16, the procedure will be easier. If necessary, the channel 15 may be empty. This makes the suction more efficient for swelling the mucous membrane H1.

In addition, the looping of the snare wire 16*b* can be repeated in the cap part 2 without pulling the endoscope 3 out of the body, since the flexible tube 9 is inserted inside the cap part 2.

Since, the opening end of the flexible tube 9 is adjacent to the inner wall of the cap part 2, when the high frequency snare 16 is protruded into the inside of the cap part 2, the loop of the snare wire 16*b* of the high frequency snare 16 widens along the inner wall of the cap part 2 as shown in FIG. 5. Therefore, the snare wire 16*b* opens to engage with the whole flange 7, so as to make the looping of the snare wire 16*b* easier. Moreover, there is another effect that when the mucous membrane H1 is sucked into the inside of the cap part 2, the sheath 16*a* does not obstruct the suction. Recently, large caps are used, in order that a larger part can be resected than before. In this case, since the interval between the channel 15 and the inner wall of the cap part 2 becomes wider, this effect is significant.

The airtight valve 10 provided at the proximal end of the flexible tube 9 prevents air from leaking on suction. Therefore, the resected part H2 of the mucous membrane H1 can be assured of being sucked and drawn into the cavity 1*a*.

The cap part 2 and the flexible tube 9 that are formed of elastic materials can be deformed corresponding to the shape of the body cavity and pass through the body cavity. This lessens patient's pain, even when the outer diameter of cap part 2 is large.

The second embodiment of the present invention is now explained with reference to the accompanying drawings. In the first embodiment and the second embodiment, like reference numerals denote like elements and a detailed description thereof is omitted.

Figure 7:
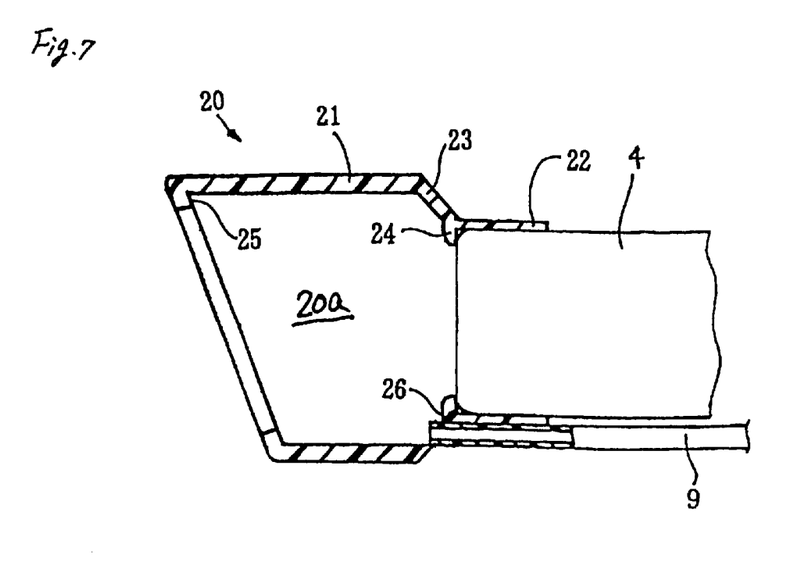
FIG. 7 is a section view showing a hood for an endoscope according to the second embodiment of the invention.
Figure 8:
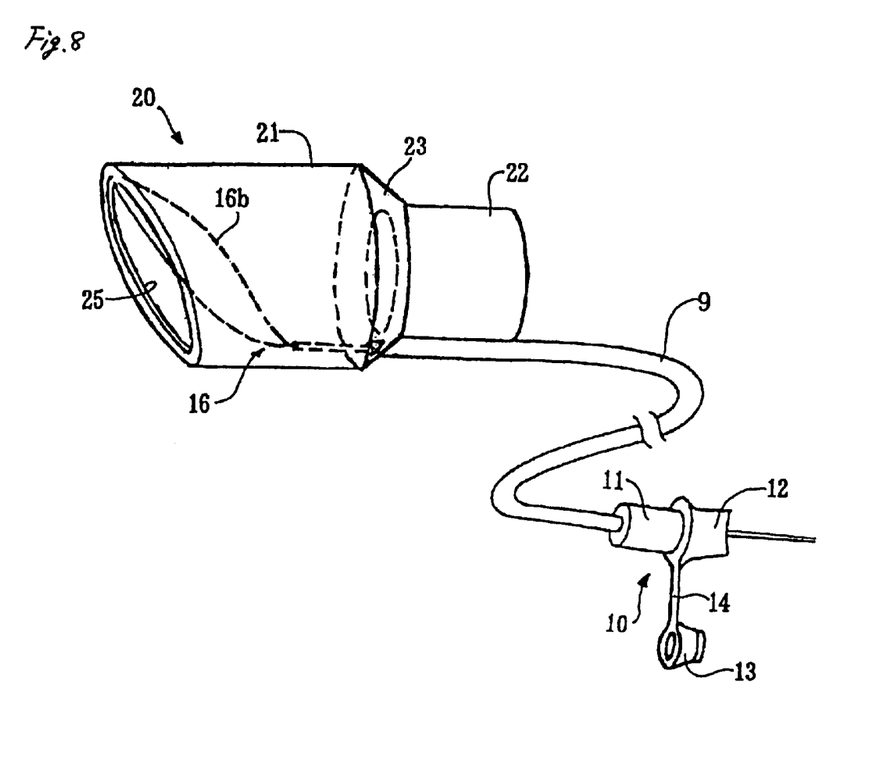
FIG. 8 is a perspective view of the hood for an endoscope according to the second embodiment of the invention.

FIGS. 7 and 8 illustrate a hood 20 for an endoscope according to the second embodiment. The hood 20 has a cap part 21 defining a cavity 20a. Preferably, the cap part 21 is approximately cylindrical and transparent. The hood 20 further comprises a substantially cylindrical endoscope mounting part 22 to detachably fix the hood 20 to the end portion of the insertion part 4 of the endoscope 3, as is the hood 1 in the first embodiment. As shown in FIG. 7, the cap part 21 and the endoscope mounting part 22 are cylindrical with different outer diameters and inner diameters. A tapered flange 23 connects the outer diameters. The outer and inner diameters and thickness and materials of the cap part 21 and the endoscope mounting part 22 and the flange 23 are set the same as in the hood according to the first embodiment.

At the distal end of the endoscope mounting part 22, an endoscope stop 24 protrudes inward towards the cavity 20a. In order to fix the hood 20 to the endoscope 3, the end of the insertion part 4 of the endoscope 3 is inserted into the endoscope mounting part 22. As shown in FIG. 7, the hood 20 is pushed until the end of the insertion part 4 of the endoscope 3 abuts the endoscope stop 24. The end of the insertion part 4 of the endoscope 3 does not go into the cap part 21, and the endoscope mounting part 22 of the hood 20 is fixed on the end of the insertion part 4 of the endoscope 3.

Also at the end of the cap part 21, a flange 25 protrudes inward. As shown in FIG. 8, a snare wire 16b let out of a sheath 16a of a high frequency snare 16 engages with the flange 25.

An opening 26 communicating with the cavity 20a of the cap part 21 is formed in the flange 23. The opening 26 is located where the axial length of the cap part 21 is shortest. Outside the endoscope mounting part 22 is arranged a flexible tube 9 into which an endoscopic treating instrument such as the high frequency snare 16 can be inserted. The end portion of the flexible tube 9 is connected to the above-mentioned opening 26. The end portion of the flexible tube 9 is fixed to the endoscope mounting part 22 and the cap part 21 in the airtight state by means of bonding, welding or the like. The end of the flexible tube 9 opens into the cavity 20a of the cap part 21.

The longitudinal axis of the flexible tube 9 and the axis of the cap part 21 are almost parallel at the connection part of the flexible tube 9 and the cap part 21. The opening end of the flexible tube 9 is adjacent to the inner wall of the cap part 21.

Furthermore, the end rim of the cap part 21 is formed along the plane that is oblique to the insertion direction of the endoscope 3.

The hood 20 is mounted on the end of the insertion part 4 of the endoscope 3. The flexible tube 9 is then fixed along the insertion part 4 of the endoscope 3 with a medical tape or the like. While this state is kept, the high frequency snare 16 is inserted into the flexible tube 9, until the tip of the high frequency snare 16 protrudes up to the cavity 20a of the cap part 21.

Next, the snare wire 16b is let out of the sheath 16a. While the tip portion of the snare wire 16b is placed on the flange 25, the snare wire 16b is pushed out, as shown in FIG. 8. This operation lets the loop of the snare wire 16b widen along the inner surface at the end of the cap part 21.

While this state is kept, the insertion part 4 of the endoscope 3 is inserted into the body, operated with an operation part which is not shown. After the opening end of the cap part 21 of the hood 20 is moved to an objective mucous membrane, the suction is started. Following operation is the same as that of the first embodiment.

In the hood 20 according to the second embodiment, the rim of the cap part 21 is oblique to the insertion direction. This makes the area of the opening end of the cap part 21 larger. Therefore, the amount of mucous membrane H1 sucked into the cavity 20a is increased. As a result, the amount of mucous membrane H1 resected at a time can increase. Also, the endoscope 3 is easily inserted into the body, since the rim is oblique.

In addition, the endoscope 3 is easily pulled out of the body, since the flange 23 is tapered.

The opening 26 connected to the flexible tube 9 is located where the axial length of the cap part 21 is shortest. This makes the tip of the high frequency snare 16 inserted in the cap part 21 reach the point on the flange where the axial length of the cap part 21 is longest. The further the opening 26 is located from the flange point which the tip of the high frequency snare 16 reaches, the easier the operation is.

The third embodiment of the present invention is now explained with reference to the accompanying drawings. In the first and third embodiments, like reference numerals denote like elements and detailed description thereof is omitted.

Figure 9:
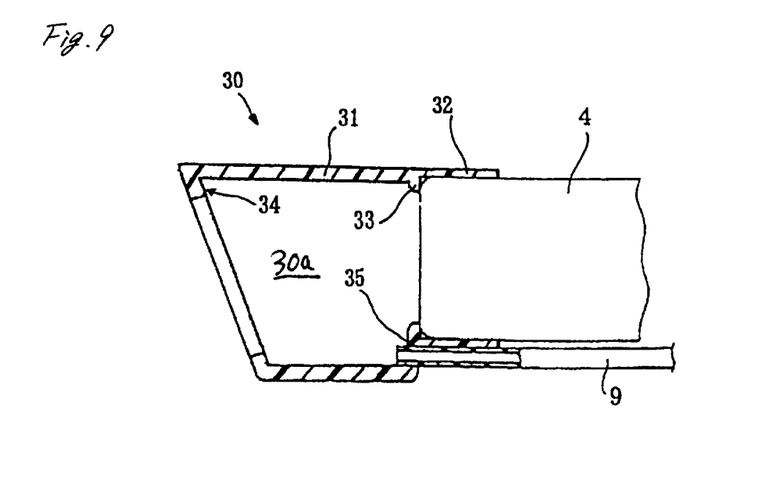
FIG. 9 is a section view showing a hood for an endoscope according to the third embodiment of the invention.

FIG. 9 shows a hood 30 for an endoscope according to the third embodiment. The hood 30 has a cap part 31 defining a cavity 30a. Preferably the cap part 31 is approximately cylindrical and transparent. The hood 30 further comprises a substantially cylindrical endoscope mounting part 32 to detachably fix the hood 30 to the end portion of the insertion part 4 of the endoscope 3, as the hoods in the first and second embodiments are fixed. As shown in FIG. 9, the cap part 31 and the endoscope mounting part 32 are cylindrical with different outer diameters and inner diameters. The center of the cap part 31 is eccentric to that of the endoscope mounting part 32. Outer and inner diameters and thickness and materials of the cap part 31 and the endoscope mounting part 32 are set the same as those of the hoods 1 and 20 according to the first and second embodiments.

At the distal end of the endoscope mounting part 32, an endoscope stop 33 protrudes inward. In order to fix the hood 30 to the endoscope 3, the end of the insertion part 4 of the endoscope 3 is inserted into the endoscope mounting part 32. As shown in FIG. 9, the hood 30 is pushed until the end of the insertion part 4 of the endoscope 3 abuts the endoscope stopper 33. The end of the insertion part 4 of the endoscope 3 does not go into the cap part 31, and the endoscope mounting part 32 of the hood 30 is fixed on the end of the insertion part 4 of the endoscope 3.

Also at the end of the cap part 31, a flange 34 protrudes inward towards the cavity 30a. The snare wire 16b let out of the sheath 16a of the high frequency snare 16 engages with the flange 34.

An opening 35 communicating with the cavity 30a of the cap part 31 is formed in a flange between the proximal end of the cap part 31 and the distal end of the endoscope mounting part 32. The opening 35 is located where the axial length of the cap part 31 is shortest. Outside the endoscope mounting part 32 is arranged a flexible tube 9 into which an endoscopic treating instrument such as the high frequency snare 16 can be inserted. The end portion of the flexible tube 9 is connected to the above-mentioned opening 35. The end portion of the flexible tube 9 is fixed to the endoscope mounting part 32 and the cap part 31 in the airtight state by means of bonding, welding or the like. The end of the flexible tube 9 opens into the cavity 30a of the cap part 31.

The other construction and operation are similar to those of the hood according to the second embodiment.

In the hood 30 according to the third embodiment, the center of the cap part 31 is eccentric to that of the endoscope mounting part 32. Therefore, the outer diameter of the cap part 31 can be as small as possible and the space for arranging the opening 35 can be secured.

Figure 10:
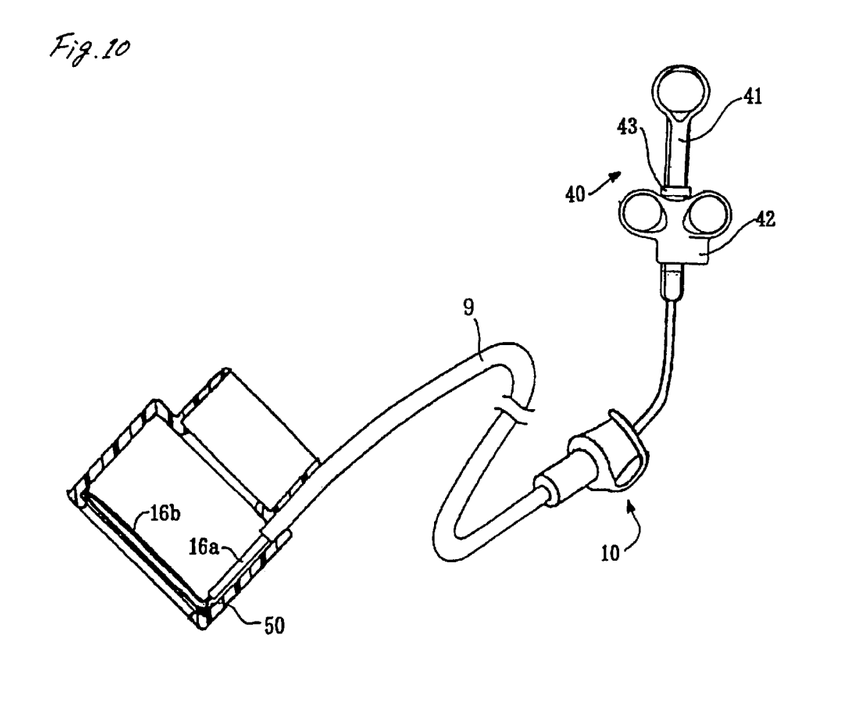
FIG. 10 is a section view showing a hood for an endoscope according to a modification of the first embodiment.

A modification of the first embodiment will now be explained with reference to FIG. 10.

In the above-mentioned first embodiment, the hood 1 is attached to the insertion part 4 of the endoscope 3. Then, after the insertion into the body, the high frequency snare 16 is inserted into the cavity 30a of the cap part 2 through the flexible tube 9.

On the other hand, in the modification, the hood 1 has the high frequency snare 16 inserted in the cap part 2 in advance. This is attached to the insertion part 4 of the endoscope 3. And the insertion part 4 is inserted into the body.

The high frequency snare 16 is previously inserted into the flexible tube 9 so that the snare wire 16b of the high frequency snare 16 reaches the inner surface of the flange 7 in the cap part 2. In this state, the snare wire 16b and the inner wall of the flange 7 is bonded with an adhesive 50 whose adhesive strength is weak. Even if an operation handle 40 which operates the snare wire 16b is operated, the snare wire 16b should not come off the inner wall of the flange 7. Viscous rubber may substitute for the adhesive 50.

The operation handle 40 includes a handle body 41 having a finger hang portion, and a slider 42 that is axially slidable with respect to the handle body 41. When the slider 42 is slid on the handle 41 axially, the snare wire 16b of the high frequency snare 16 axially slides with respect to the sheath 16a to control the opening of the snare wire 16b.

In the modification, a control member 43 is provided to control sliding of the slider 42, so that the snare wire 16b will not retract until the product is shipped and used by an operator. The control member 43 is detachably attached to the handle body 41 and removed from the handle body 41 just before the operation of the high frequency snare 16. This prevents the slider 42 from moving inadvertently.

As mentioned above, according to the modification, an operator can obtain a hood for an endoscope in which the snare wire 16b of the high frequency snare 16 is opened in the cap part 2 in advance. This makes preparation for an operation easier and contributes to the operation improvement.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A hood for an endoscope comprising:
   a cap part defining a cavity and having an opening;
   a fixing part for fixing said cap part to a distal end of an endoscope; and
   a flexible tube having a distal end which is fixed to said cap part and communicating with the cavity of said cap part through the opening, and a proximal end through which an endoscopic treating instrument can be removably inserted into the flexible tube without connecting a tube arranged inside the endoscope thereto;
   wherein said flexible tube is adapted to be arranged outside the endoscope when said hood is attached at the distal end of the endoscope;
   wherein the cap part includes a side wall and a connecting wall which connects between the side wall and the fixing part, and outwardly extends from the fixing part; and
   wherein the opening is formed on the connecting wall.

2. The hood according to claim 1, wherein said cap part and said fixing part are substantially cylindrical to be fitted on the distal end of said endoscope which is also substantially cylindrical.

3. The hood according to claim 2, wherein the outer diameter of said cap part is greater than the outer diameter of said fixing part.

4. The hood according to claim 3, further comprising a flange-shaped connecting portion which connects a proximal end of said cap part and a distal end of said fixing part.

5. The hood according to claim 1, wherein said cap part is made from a flexible resin.

6. The hood according to claim 1, wherein a protrusion projecting inward toward the cavity is formed on the inner surface of said cap part.

7. The hood according to claim 6, wherein said protrusion is located near a rim of said cap part.

8. The hood according to claim 6, wherein said protrusion protrudes inward as a flange.

9. The hood according to claim 6, wherein a snare wire of a high frequency snare is pushed against and located on a proximal surface of said protrusion.

10. The hood according to claim 9, wherein said high frequency snare is set against the proximal surface of said protrusion before said endoscope is inserted into the body.

11. The hood according to claim 1, wherein an abutment protruding inward is provided on an inner surface of a boundary between said cap part and said fixing part.

12. The hood according to claim 11, wherein said abutment protrudes inward as a flange.

13. The hood according to claim 1, wherein a rim of said cap part is in a plane which is oblique to an insertion direction of the endoscope.

14. The hood according to claim 13, wherein said flexible tube communicates with said cap part at a position where an axial length of the cap part is shortest.

15. The hood according to claim 1, wherein a rim of said cap part is in a plane which is perpendicular to an insertion direction of the endoscope.

16. The hood according to claim 1, wherein said flexible tube has a valve for preventing fluid from flowing from the proximal side to the distal side.

17. The hood according to claim 16, wherein said valve is provided at the proximal end of said flexible tube.

18. A hood for an endoscope comprising:
   a cap part defining a cavity and having an opening;
   a fixing part for fixing said cap part to a distal end of an endoscope; and a flexible tube having a distal end which is fixed to said cap part and communicating with the cavity of said cap part;

wherein said flexible tube is adapted to be arranged outside an endoscope when said hood is attached at the distal end of the endoscope;

wherein the cap part includes a side wall and a connecting wall which connects between the side wall and the fixing part, and outwardly extends from the fixing part; and wherein the opening is formed on the connecting wall.

19. An endoscopic hood system comprising:

a cap part defining a cavity and having an opening;

a fixing part for fixing said cap part to a distal end of an endoscope;

a flexible tube having a distal end which is fixed to said cap part and communicating with the cavity of said cap part through said opening, and a proximal end; and an endoscopic treating instrument being removably inserted into said flexible tube through said proximal end without connecting a tube arranged inside the endoscope thereto;

wherein said flexible tube is adapted to be arranged outside an endoscope when said hood is attached at the distal end of the endoscope;

wherein the cap part includes a side wall and a connecting wall which connects between the side wall and the fixing part and outwardly extends from the fixing part; and wherein the opening is formed on the connecting wall.

20. An endoscopic hood system according to claim 19, wherein said endoscopic treating instrument is a high frequency snare.

21. An endoscopic hood system according to claim 19, wherein said endoscopic treating instrument is an injection needle.

22. A hood for an endoscope comprising:

a cap part defining a cavity and having an opening;

a fixing part for fixing said cap part to a distal end of an endoscope; and a flexible tube having a distal end which is fixed to said cap part and communicating with the cavity of said cap part through the opening, and a proximal end through which an endoscopic treating instrument can be removably inserted into the flexible tube without connecting a tube arranged inside the endoscope thereto;

wherein said flexible tube is adapted to be arranged outside the endoscope when said hood is attached at the distal end of the endoscope, said cap part and said fixing part are substantially cylindrical to be fitted on the distal end of said endoscope which is also substantially cylindrical, wherein the outer diameter of said cap part is greater than the outer diameter of said fixing part, and the center of said cap part is eccentric to that of said fixing part.

23. A hood for an endoscope comprising:

a cap part defining a cavity and having an opening;

a fixing part for fixing said cap part to a distal end of an endoscope;

a flexible tube having a distal end which is fixed to said cap part and communicating with the cavity of said cap part through the opening, and a proximal end through which an endoscopic treating instrument can be removably inserted into the flexible tube without connecting a tube arranged inside the endoscope thereto; and a flange-shaped connecting portion which connects a proximal end of said cap part and a distal end of said fixing part;

wherein said flexible tube is adapted to be arranged outside the endoscope when said hood is attached at the distal end of the endoscope, said cap part and said fixing part are substantially cylindrical to be fitted on the distal end of said endoscope which is also substantially cylindrical, wherein the outer diameter of said cap part is greater than the outer diameter of said fixing part, and said connecting portion is tapered.

24. A hood for an endoscope comprising:

a cap part defining a cavity and having an opening;

a fixing part for fixing said cap part to a distal end of an endoscope;

a flexible tube having a distal end which is fixed to said cap part and communicating with the cavity of said cap part through the opening, and a proximal end through which an endoscopic treating instrument can be removably inserted into the flexible tube without connecting a tube arranged inside the endoscope thereto; and a flange-shaped connecting portion which connects a proximal end of said cap part and a distal end of said fixing part;

wherein said flexible tube is adapted to be arranged outside the endoscope when said hood is attached at the distal end of the endoscope, said cap part and said fixing part are substantially cylindrical to be fitted on the distal end of said endoscope which is also substantially cylindrical, wherein the outer diameter of said cap part is greater than the outer diameter of said fixing part, and the distal end of said flexible tube is connected to said connecting portion.

* * * * *